United States Patent [19]

Noble

[11] 4,444,748

[45] Apr. 24, 1984

[54] USE OF TARTRATES IN TREATMENT OF HERPES

[76] Inventor: Rudolf E. Noble, 1867 Broadway, San Francisco, Calif. 94109

[21] Appl. No.: 442,132

[22] Filed: Nov. 16, 1982

[51] Int. Cl.³ .................................................. A61K 31/19
[52] U.S. Cl. ........................................................ 424/317
[58] Field of Search .......................................... 424/317

[56] References Cited

U.S. PATENT DOCUMENTS 3,567,657  3/1971  Lichtenstein .................. 424/317 X
3,879,537  4/1975  Van Scott et al. .................. 424/311

*Primary Examiner*—Leonard Schenkman
*Attorney, Agent, or Firm*—Owen, Wickersham & Erickson

[57] ABSTRACT

A herpes treatment found effective in quickly healing lesions includes a tartrate, such as potassium bitartrate.

7 Claims, No Drawings

USE OF TARTRATES IN TREATMENT OF HERPES

BACKGROUND OF THE INVENTION

Herpes viruses, particularily those members of Class 4 (Herpes Simplex Type I (labialis) and Herpes Simplex Type II (genitalis)), have now caused a major U.S. epidemic problem. Government estimates suggest that between 5 and 20 million Americans may be affected by the Herpes Simplex virus with as many as 500,000 new cases reported each year. Some experts say as many as 20% of young adults may have herpes.

Herpes genitalis is the second most common venereal disease and it is predicted to soon become the most prevalent. Estimates show that herpetic infections will double in the next few years. The lesions appear as crusted vesicles on the genitalia of either sex, which often are painful, transmittable and usually take about two weeks to disappear.

Herpes labialis ("fever blisters", "cold sores") infections usually start out with a prodroma characteristically felt as a tingling sensation on the lips or face. Within a short time, vesicles are noted in the affected area which subsequently can expand to cover fairly large orofacial areas. These vesicles usually break and can cause secondary infections leaving an ulcerated area which scabs and heals in about two weeks.

The applicant has been bothered with herpes labialis infections for about 25 years. He has tried a host of medical remedies, all with no success. These include: UV-dye inactivation of the virus, smallpox injections, ingestion of large doses of lactobacillus casei tablets, "Blistex", ether compresses to the lesions, etc. He has also tried many "home remedies" including use of baking soda, chlorine bleach, yogurt compresses, watermelon, seaweed, earwax, etc., with no success.

SUMMARY OF THE INVENTION

Through trial and error, however, I have found an agent that markedly decreases the time required for healing of herpetic lesions. This involves the simple application, topically, of a common food spice (cream of tartar) to the lesions at the outset of any feeling of prodrome, which is usually a tingling, burning, and/or itching sensation in the area to be affected. I have tried this treatment on my own last seven outbreaks in the past year, with a marked reduction in the time required for healing. The lesions, in the past, have generally taken at least fourteen days to heal. However, with the liberal and frequent daily application (at least five times a day) of the treatment according to my invention, the lesions usually cure within three days. In addition, the lesions are not nearly as large, uncomfortable, or unsightly as they were in the past.

DESCRIPTION OF PREFERRED EMBODIMENT

The treatment comprises cream of tartar, most advantageously mixed in a base such as coconut oil, preferably in a 1:1 weight ratio, for ease of application.

The active ingredient of cream of tartar is potassium bitartrate $KH(C_4H_4O_6)$; the potassium acid salt of tartaric acid. Tartaric acid is a reducing agent and it is conceivable that it might in some way react with the nucleic acids of the herpes simplex virus to inhibit its activation or replication. Cream of tartar preparations have been used in the past for other, unrelated medical purposes.

EXAMPLE I

Small herpetic lesions were noted on the left corner of the lower lip of a patient one morning. Subsequently, straight cream of tartar was applied to the affected area at least four times each day. The vesicles never grew any larger and were completely gone within four days after they were first noted.

EXAMPLE II

Herpetic lesions were discovered starting to form on the right corner of the same patient's upper lip on another occasion several months later. Cream of tartar was applied liberally. The next day the lesions covered an area approximately ¾ cm. in diameter. On the evening of the next day following, the lesions had disappeared and at no time did they cause any significant disfigurement or discomfort.

EXAMPLE III

Several months later, after a full day's exposure to the sun, the same patient felt a tingling sensation (the usual prodrome) all over his lips. He immediately applied a treatment comprising cream of tartar and coconut oil in a 1:1 mixture, and no hepetic lesions ever developed.

EXAMPLE IV

Ten days after the previous episode of Example III, the same patient noted the onset of a few vesicles on the left corner of his lower lip. He immediately applied the herpes treatment used in Example III. The lesions disappeared by the next day.

As shown by the examples, the herpes treatment of the invention is highly effective against herpes labialis, and will undoubtedly also be effective against the very similar herpes genitalis virus and other herpetic viruses, i.e. Epstein-Barr virus, varicella zoster virus (shingles), and cytomegalic virus.

It is believed that the tartrate moiety may be responsible for the healing effect of the herpes treatment of the invention. Thus, in place of cream of tartar the herpes treatment may include tartaric acid, sodium bitartrate, or other salts and esters and derivatives involving the tartrate moiety.

The inactive carrier included in the herpes treatment of the invention may be coconut oil as disclosed above, which is beneficial cosmetically and aids in the application of the treatment. Other inactive carriers may be used alternatively. Preferably an oily carrier is used, but the carrier may be non-oily. Alternative carriers include, inter alia, water, alcohol, lanolin, almond oil, cocoa butter, pork lard, glycerine, mineral oil, petroleum jelly, hydrophilic base, aquaphor, and eucerin.

The embodiment described is for illustration of the principles of the invention and is not intended to be limiting of the invention's scope. Variations to the preferred embodiment will be apparent to those skilled in the art and may be made without departing from the scope of the invention as defined in the following claims.

I claim:

1. A method for treating herpes virus lesions, comprising applying an effective amount of a composition including potassium bitartrate mixed with an oily carrier medium topically to the affected area commencing soon after prodrome is felt.

2. The method of claim 1, including applying the composition at least five times daily.

3. The method of claim 1, wherein the oily medium is coconut oil.

4. The method of claim 3, the potassium bitartrate and coconut oil being present in approximately equal proportions by weight.

5. A method for treating herpes virus lesions, comprising applying topically to the affected area an effective amount of composition including potassium bitartrate commencing soon after the first sign of the onslaught of a lesion.

6. The method of claim 5, wherein composition is applied at least five times daily.

7. The method of claim 5, wherein the composition includes an oily carrier medium selected from the group consisting of coconut oil, lanolin, almond oil, glycerine, and petroleum jelly.

* * * * *